(12) United States Patent
Michaelis et al.

(10) Patent No.: US 7,598,282 B2
(45) Date of Patent: Oct. 6, 2009

(54) NEUROPROTECTIVE AGENTS

(75) Inventors: Mary Louise Michaelis, Lawrence, KS (US); Ingrid Gunda Georg, Lawrence, KS (US); Richard H. Himes, Lawrence, KS (US); Kenneth L. Audus, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 105 days.

(21) Appl. No.: 11/591,093

(22) Filed: Nov. 1, 2006

(65) Prior Publication Data

US 2007/0099971 A1 May 3, 2007

Related U.S. Application Data

(60) Provisional application No. 60/732,074, filed on Nov. 1, 2005.

(51) Int. Cl.
*A61K 31/424* (2006.01)
*C07D 498/02* (2006.01)

(52) U.S. Cl. ...................... 514/375; 548/218

(58) Field of Classification Search ............... 514/375, 514/368; 548/218, 154
See application file for complete search history.

(56) References Cited

U.S. PATENT DOCUMENTS 6,046,177 A * 4/2000 Stella et al. ............... 514/58

FOREIGN PATENT DOCUMENTS

JP      08-325147      12/1996

OTHER PUBLICATIONS

Darabantu et al., 3,7-Dioxa-1-azabicyclo[3.3.0]octanes Substituted at the C-5 Position—From Local to Global Stereochemistry, 2004, Eur. J. Org. Chem., p. 2645.*
Shintani et al., *GS-164, a small synthetic compound, stimulates tubulin polymerization by a similar mechanism to that of Taxol,* Cancer Chemother Pharmacol 40, 513-520 (1997).
Michaelis et al., *Amyloid Peptide Toxicity and Microtubule-Stabilizing Drugs,* Journal of Molecular Neuroscience 19, 101-105 (2002).

* cited by examiner

*Primary Examiner*—Kamal A Saeed
*Assistant Examiner*—Kristin Bianchi
(74) *Attorney, Agent, or Firm*—Stinton Morrison Hecker LLP

(57) ABSTRACT

Novel stereoisomers of GS-164 are provided. The compounds, such as (3R,5S,7as)-(3,5-bis(4-fluorophenyl)tetrahydro-1H-oxazolo[3,4-c]oxazol-7a-yl)methanol (TH-237A) and (3R,5S,7as)-(3,5-bis(4-fluorophenyl)tetrahydro-1H-oxazolo[3,4-c]oxazol-7a-yl)methanol (TH-242A) exhibit neuroprotective effects via a mechanism that does not involve microtubule stabilization.

19 Claims, 6 Drawing Sheets

TH-237A  TH-236B

TH-242A  TH-242B

NEUROPROTECTIVE AGENTS

CROSS-REFERENCE TO RELATED APPLICATIONS

This application is based on and claims priority to U.S. Provisional Application Ser. No. 60/732,074, filed on Nov. 1, 2005, which is hereby incorporated herein by reference.

STATEMENT REGARDING FEDERALLY SPONSORED RESEARCH OR DEVELOPMENT

Not applicable.

BACKGROUND OF THE INVENTION

Paclitaxel (Taxol®) is a therapeutic agent with antitumor activity against ovarian, breast, and lung carcinomas. The compound is extracted from the bark of the Pacific yew tree *Taxus brevifolia*, as well as from needles and stems of this and other *Taxus* species, and its complex chemical structure has been determined. Interest in this compound arises from not only its clinical activity against poorly responsive solid tumors but also from its unique mechanism of action. Paclitaxel promotes tubulin polymerization and stabilizes microtubules that result in the inhibition of cell migration and chromosome segregation by blocking the transit of cycling cells in the G2/M phase. More recently, paclitaxel has been proposed as a therapeutic for stabilizing microbules in the brain cells of individuals who are deficient in normal tau proteins, for example in individuals suffering from Alzheimer's Disease. See Trojanowski et al., U.S. Pat. No. 5,580,898.

In 1997, a group of Japanese researchers described a novel small synthetic compound designated GS-164, which was reported to stimulate tubulin polymerization and stabilize microtubules. See Shintani et al., *GS-164, a small synthetic compound, stimulates tubulin polymerization by a similar mechanism to that of Taxol*, Cancer Chemother Pharmacol 40:513-520 (1997); Japanese Patent No. 8-325147 (1996). The researchers reported that GS-164 has activities similar to those of paclitaxel in vitro and in vivo, even thought it was structurally unrelated. The compound was reported to stimulate tubulin polymerization with one-tenth the activity of paclitaxel. According to the authors, the stereoisomer of GS-164 that was responsible for its microtubule-stabilizing effects was determined to be the R/R isomer, which mimicked the structure of paclitaxel.

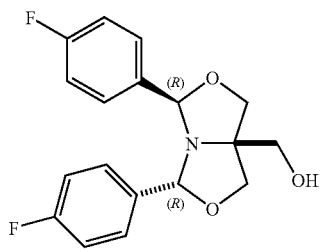

R/R isomer GS-164 (Shintani 1997)

(3R,5R)-(3,5-bis(4-fluorophenyl)tetrahydro-1H-oxazolo[3,4-c]oxazol-7a-yl)methanol Several years later, some of the present inventors conducted preliminary studies on the effects of several purported microtubule stabilizing agents, including paclitaxel and GS-164, in beta amyloid induced cell death in primary neurons. See Michaelis et al, *Amyloid Peptide Toxicity and Microtubule-Stabilizing Drugs*, Journal of Molecular Neuroscience, 19, 101-105, (2002). The GS-164 used in these experiments was a mixture of stereoisomers that had been produced according to Shintani (1997).

In the present invention, a novel stereoisomer of GS-164 denominated TH-237A has been isolated, and it exhibits neuroprotective effects. Moreover, it was shown that this novel stereoisomer surprisingly does not stimulate tubulin polymerization as reported with respect to the (R/R) GS-164 stereoisomer. Moreover, the novel stereoisomer shows significant uptake by the brain. Thus, the present invention is directed to novel compositions comprising substantially pure stereoisomers, as well as methods of using these stereoisomers as neuroprotective agents.

BRIEF SUMMARY OF THE INVENTION

The present invention is directed novel stereoisomers and stereomerically pure compounds. In one aspect, the stereoisomers have the Formula I:

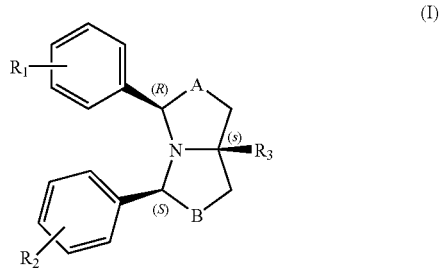

wherein A and B are sulfur or oxygen; wherein $R_1$ and $R_2$ are independently halogen, alkyl, alkoxy, haloalkyl; and wherein $R_3$ is alcohol. It will be appreciated that $R_1$ and $R_2$ may independently be in the para, meta, or ortho position.

In an preferred aspect, stereoisomers according to

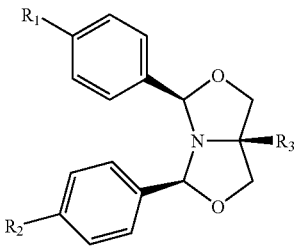

are provided wherein $R_1$ and $R_2$ are independently halogen, alkyl, alkoxy, haloalkyl; and wherein $R_3$ is alcohol. For example, the inventive stereoisomers may be selected from (3R,5S,7as)-(3,5-bis(4-fluorophenyl)tetrahydro-1H-oxazolo[3,4-c]oxazol-7a-yl)methanol (TH-237A); (3R,5S,7as)-(3,5-bis(4-trifluoromethylphenyl)tetrahydro-1H-oxazolo[3,4-c]oxazol-7a-yl)methanol (TH-242A); (3R,5S,7as)-(3,5-bis(4-difluoromethylphenyl)tetrahydro-1H-oxazolo[3,4-c]oxazol-7a-yl)methanol; (3R,5S,7as)-(3,5-bis(4-fluoromethylphenyl)tetrahydro-1H-oxazolo[3,4-c]oxazol-7a-yl)methanol; (3R,5S,7as)-(3,5-bis(4-chlorophenyl)

tetrahydro-1H-oxazolo[3,4-c]oxazol-7a-yl)methanol; (3R, 5S,7as)-(3,5-bis(4-methylphenyl)tetrahydro-1H-oxazolo[3, 4-c]oxazol-7a-yl)methanol; (3R,5S,7as)-(3,5-bis(4-methoxyphenyl)tetrahydro-1H-oxazolo[3,4-c]oxazol-7a-yl) methanol; (3R,5S,7as)-(3,5-bis(4-fluorophenyl)tetrahydro-1H-oxazolo[3,4-c]oxazol-7a-yl)ethanol; (3R,5S,7as)-(3,5-bis(4-trifluoromethylphenyl)tetrahydro-1H-oxazolo[3,4-c]oxazol-7a-yl)ethanol; (3R,5S,7as)-(3,5-bis(4-difluoromethylphenyl)tetrahydro-1H-oxazolo[3,4-c]oxazol-7a-yl)ethanol; (3R,5S,7as)-(3,5-bis(4-fluoromethylphenyl) tetrahydro-1H-oxazolo[3,4-c]oxazol-7a-yl)ethanol; (3R,5S, 7as)-(3,5-bis(4-chlorophenyl)tetrahydro-1H-oxazolo[3,4-c] oxazol-7a-yl)ethanol; (3R,5S,7as)-(3,5-bis(4-methylphenyl) tetrahydro-1H-oxazolo[3,4-c]oxazol-7a-yl)ethanol; and (3R, 5S,7as)-(3,5-bis(4-methoxyphenyl)tetrahydro-1H-oxazolo [3,4-c]oxazol-7a-yl)ethanol.

In still another aspect, inventive stereoisomers are selected from the group consisting of (3R,5S,7as)-(3,5-bis(3-fluorophenyl)tetrahydro-1H-oxazolo[3,4-c]oxazol-7a-yl)methanol; (3R,5S,7as)-(3,5-bis(3-trifluoromethylphenyl)tetrahydro-1H-oxazolo[3,4-c]oxazol-7a-yl)methanol; (3R,5S,7as)-(3,5-bis(3-difluoromethylphenyl)tetrahydro-1H-oxazolo[3, 4-c]oxazol-7a-yl)methanol; (3R,5S,7as)-(3,5-bis(3-fluoromethylphenyl)tetrahydro-1H-oxazolo[3,4-c]oxazol-7a-yl)methanol; (3R,5S,7as)-(3,5-bis(3-chlorophenyl) tetrahydro-1H-oxazolo[3,4-c]oxazol-7a-yl)methanol; (3R, 5S,7as)-(3,5-bis(3-methylphenyl)tetrahydro-1H-oxazolo[3, 4-c]oxazol-7a-yl)methanol; (3R,5S,7as)-(3,5-bis(3-methoxyphenyl)tetrahydro-1H-oxazolo[3,4-c]oxazol-7a-yl) methanol; (3R,5S,7as)-(3,5-bis(3-fluorophenyl)tetrahydro-1H-oxazolo[3,4-c]oxazol-7a-yl)ethanol; (3R,5S,7as)-(3,5-bis(3-trifluoromethylphenyl)tetrahydro-1H-oxazolo[3,4-c] oxazol-7a-yl)ethanol; (3R,5S,7as)-(3,5-bis(3-difluoromethylphenyl)tetrahydro-1H-oxazolo[3,4-c]oxazol-7a-yl)ethanol; (3R,5S,7as)-(3,5-bis(3-fluoromethylphenyl) tetrahydro-1H-oxazolo[3,4-c]oxazol-7a-yl)ethanol; (3R,5S, 7as)-(3,5-bis(3-chlorophenyl)tetrahydro-1H-oxazolo[3,4-c] oxazol-7a-yl)ethanol; (3R,5S,7as)-(3,5-bis(3-methylphenyl) tetrahydro-1H-oxazolo[3,4-c]oxazol-7a-yl)ethanol; and (3R, 5S,7as)-(3,5-bis(3-methoxyphenyl)tetrahydro-1H-oxazolo [3,4-c]oxazol-7a-yl)ethanol.

In still another aspect, inventive stereoisomers are selected from the group consisting of (3R,5S,7as)-(3,5-bis(2-fluorophenyl)tetrahydro-1H-oxazolo[3,4-c]oxazol-7a-yl)methanol; (3R,5S,7as)-(3,5-bis(2-trifluoromethylphenyl)tetrahydro-1H-oxazolo[3,4-c]oxazol-7a-yl)methanol; (3R,5S,7as)-(3,5-bis(2-difluoromethylphenyl)tetrahydro-1H-oxazolo[3, 4-c]oxazol-7a-yl)methanol; (3R,5S,7as)-(3,5-bis(2-fluoromethylphenyl)tetrahydro-1H-oxazolo[3,4-c]oxazol-7a-yl)methanol; (3R,5S,7as)-(3,5-bis(2-chlorophenyl) tetrahydro-1H-oxazolo[3,4-c]oxazol-7a-yl)methanol; (3R, 5S,7as)-(3,5-bis(2-methylphenyl)tetrahydro-1H-oxazolo[3, 4-c]oxazol-7a-yl)methanol; (3R,5S,7as)-(3,5-bis(2-methoxyphenyl)tetrahydro-1H-oxazolo[3,4-c]oxazol-7a-yl) methanol; (3R,5S,7as)-(3,5-bis(2-fluorophenyl)tetrahydro-1H-oxazolo[3,4-c]oxazol-7a-yl)ethanol; (3R,5S,7as)-(3,5-bis(2-trifluoromethylphenyl)tetrahydro-1H-oxazolo[3,4-c] oxazol-7a-yl)ethanol; (3R,5S,7as)-(3,5-bis(2-difluoromethylphenyl)tetrahydro-1H-oxazolo[3,4-c]oxazol-7a-yl)ethanol; (3R,5S,7as)-(3,5-bis(2-fluoromethylphenyl) tetrahydro-1H-oxazolo[3,4-c]oxazol-7a-yl)ethanol; (3R,5S, 7as)-(3,5-bis(2-chlorophenyl)tetrahydro-1H-oxazolo[3,4-c] oxazol-7a-yl)ethanol; (3R,5S,7as)-(3,5-bis(2-methylphenyl) tetrahydro-1H-oxazolo[3,4-c]oxazol-7a-yl)ethanol; and (3R, 5S,7as)-(3,5-bis(2-methoxyphenyl)tetrahydro-1H-oxazolo [3,4-c]oxazol-7a-yl)ethanol.

The stereoisomers of the present invention are useful for treating neurodegenerative disorders, such as amyloidosis disorders. In one aspect, a method for treating a neurodegenerative disorder is provided which comprises administering to a patient in need of such treatment a therapeutically effective amount of a stereoisomer of the present invention. A preferred stereoisomer is (3R,5S,7as)-(3,5-bis(4-fluorophenyl)tetrahydro-1H-oxazolo[3,4-c]oxazol-7a-yl)methanol (TH-237A) or (3R,5S,7as)-(3,5-bis(4-trifluoromethylphenyl)tetrahydro-1H-oxazolo[3,4-c]oxazol-7a-yl)methanol (TH-242A) or a prodrug thereof. The stereoisomers may be administered parenterally, transdermally, mucosally, nasally, buccally, sublingually, or orally. In addition, the stereoisomers may be associated with pharmaceutically acceptable excipients. In one aspect, the stereoisomers are complexed with a cyclodextrin (e.g. Captisol®).

The stereoisomers of the present invention also surprisingly do not stabilize microtubules, as evidenced by tubulin centrifugation assays, multi-well plate assays, and/or cold stability experiments discussed herein. For example, in one aspect, the compounds of the present invention promote less than about 20%, 10%, or 5% of tubulin polymerization at a 200 µM concentration using the tubulin assembly centrifugation assay. In another aspect, the stereoisomers of the present invention are two, three, or four times less potent than paclitaxel in promoting tubulin polymerization when using a multi-well plate assay. In still another aspect, cold stability experiments show that the stereoisomers of the present invention prevent depolymerization only about 20, 10 or 5% of microtubules at concentrations around 400 µM In still another aspect, the stereoisomers of the present invention are shown not to inhibit tubulin polymerization as evidenced by radiolabeling the compounds, competitive binding, and/or immunostaining as discussed herein.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1A:
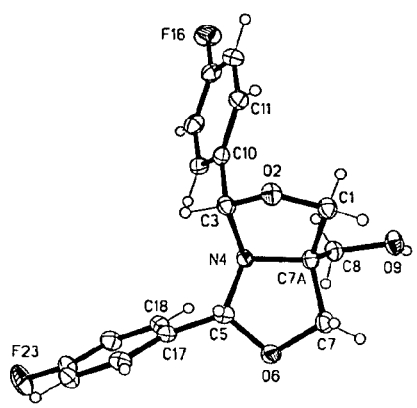
FIG. 1(A) is an ellipsoid drawing of the molecular structure of TH-237A and TH-236B (one enantiomer shown) from x-ray diffraction studies.
Figure 1A:
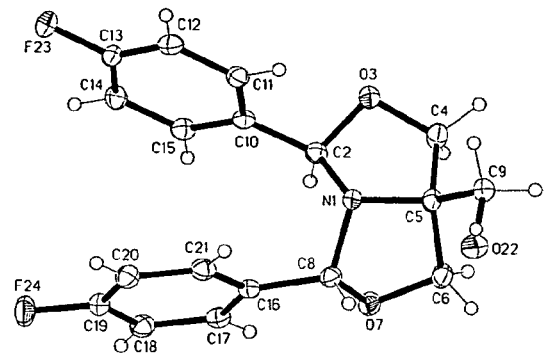
Figure 1B:
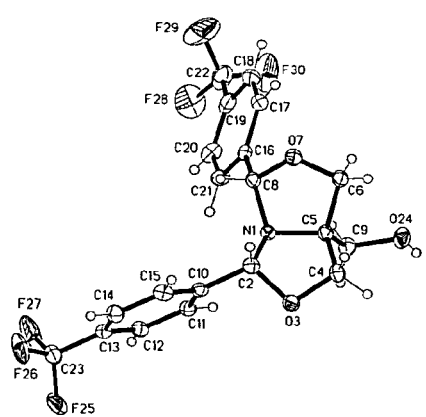
FIG. 1(B) is an ellipsoid drawing of the molecular structure of TH-242A and TH-242B (one enantiomer shown) from x-ray diffraction studies.
Figure 1B:
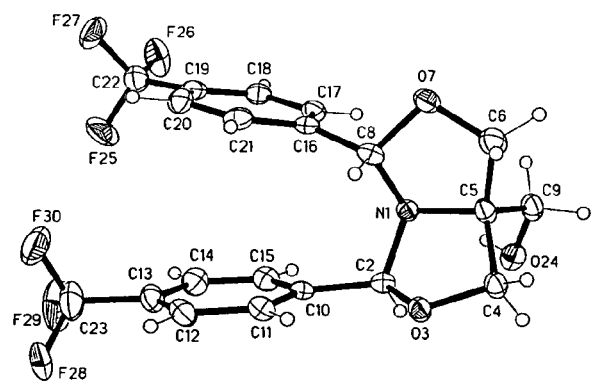

The present invention is directed to novel stereoisomers having the Formula I:

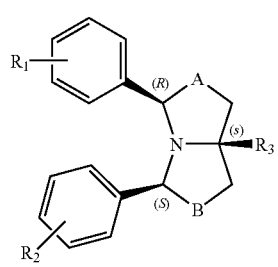

(I)

wherein A and B are sulfur or oxygen; wherein $R_1$ and $R_2$ are independently halogen, alkyl, alkoxy, haloalkyl; and wherein $R_3$ is alcohol. $R_1$ and $R_2$ may independently be in the para, meta, or ortho position.

A preferred composition comprises stereomerically pure (3R,5S,7as)-(3,5-bis(4-fluorophenyl)tetrahydro-1H-oxazolo[3,4-c]oxazol-7a-yl)methanol (TH-237A) or stereomerically pure (3R,5S,7as)-(3,5-bis(4-trifluoromethylphenyl)tetrahydro-1H-oxazolo[3,4-c]oxazol-7a-yl)methanol (TH-242A). The composition preferably substantially free of (3R,5R)-(3,5-bis(4-fluorophenyl)tetrahydro-1H-oxazolo[3,4-c]oxazol-7a-yl)methanol and (3S,5S)-(3,5-bis(4-fluorophenyl)tetrahydro-1H-oxazolo[3,4-c]oxazol-7a-yl)methanol. The compositions are useful as neuroprotective agents, and in the treatment of neurodegenerative disorders.

Further, the invention includes the use of stereomerically pure (3R,5S,7as)-(3,5-bis(4-fluorophenyl)tetrahydro-1H-oxazolo[3,4-c]oxazol-7a-yl)methanol (TH-237A), in combination with one or more other therapeutic agents for the treatment of a neurodegenerative disorder, including, but not limited to those involving beta amyloids. The compositions administered in each of these methods may be concurrent, sequential, or in any combination of concurrent or sequential.

Further, the invention includes the use of stereomerically pure (3R,5S,7as)-(3,5-bis(4-trifluoromethylphenyl)tetrahydro-1H-oxazolo[3,4-c]oxazol-7a-yl)methanol (TH-242A), in combination with one or more other therapeutic agents for the treatment of a neurodegenerative disorder, including, but not limited to those involving beta amyloids. The compositions administered in each of these methods may be concurrent, sequential, or in any combination of concurrent or sequential.

As used herein, the term "alkyl" embraces branched or unbranched saturated hydrocarbon group of one to 10 carbon atoms, such as methyl, ethyl, n-propyl, isopropyl, n-butyl, isobutyl, t-butyl, octyl, decyl, and the like. "Lower alkyl" refers to an alkyl group of one to six, more preferably one to four, carbon atoms.

The term "alkoxy" embraces oxy-containing groups substituted with an alkyl group. Examples include, without limitation, methoxy, ethoxy, and tert-butoxy. Most preferred are "lower alkoxy" groups having one to six carbon atoms. Examples of such groups include methoxy, ethoxy, propoxy, butoxy, isopropoxy, and tert-butoxy.

As used herein, the term "alcohol" embraces an alkyl group having one or more hydroxy (—OH) substituents. Primary, secondary, and tertiary alcohols are contemplated, such as mono-alcohols as well as polyhydroxy variants. Preferred alcohols are those containing from about one up to six carbon atoms. Exemplary of preferred aliphatic alcohols are: methanol, ethanol, 1-propanol, 2-propanol, 1-propen-2-ol, 1-butanol, 2-butanol, 2-methyl-2-propanol, 1-pentanol, 2-pentanol, 3-pentanol, and 3-methyl-1-butanol. Of the alcohols, methanol is most preferred.

As used herein, the term "halo" or "halogen" embraces to fluoro, chloro, bromo, or iodo, usually regarding halo substitution for a hydrogen atom in an organic compound. Of the halogens, fluorine is the most preferred.

As used herein, the term "haloalkyl" refers to an alkyl group having at least one halogen thereon. The term includes monohaloalkyl, dihaloalkyl, and trihaloalkyl groups. Examples of haloalkyl groups include fluoromethyl, difluoromethy, trifluoromethyl, fluoroethyl, pentafluoroethyl, 2,2,2-trifluoroethyl, and 2,2,3,3,3-pentafluoropropyl. Preferably, the haloalkyl comprises trifluoromethyl.

As used herein, the term "stereoisomers" is a general term for all isomers of individual molecules that differ only in the orientation of their atoms in space. The term includes enantiomers and diastereoisomers. The term "diastereoisomers" refers to stereoisomers that are not mirror images of one another, while the term "enantiomers" refers to stereoisomers that are mirror images of each other and are nonsuperimposeable.

The term "stereomerically pure" refers to a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereoisomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. In a preferred aspect, the stereomerically pure compounds preferably have none of the (R/R) stereoisomer or the (S/S) stereoisomer.

The term "racemic" refers to a mixture of equal parts of enantiomers and which is optically inactive. For example, TH-236B comprises a racemic mixture of the (R/R) and (S/S) enantiomers.

The term "neuroprotection" refers to inhibition of progressive deterioration of neurons that leads to cell death.

The term "neurodegenerative disorder" refers to a disorder in which progressive loss of neurons occurs either in the peripheral nervous system or in the central nervous system. Examples of neurodegenerative disorders include, but are not limited to chronic neurodegenerative diseases such as diabetic peripheral neuropathy, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoff's related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica and frontal lobe dementia. Also other neurodegenerative disorders resulting from cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

Preferably, the neurodegenerative disorder is selected from Alzheimer's disease, Parkinson's disease, amyotrophic lateral sclerosis, age-related memory loss, senility and age-related dementia, most preferably, the neurodegenerative disorder is Alzheimer's disease. Because, most preferably, the neurodegenerative disorder is Alzheimer's disease, also defined as an amyloidosis, other conditions within the methods of the present invention include other amyloidosis disorders which share features including, but not limited to, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

As used herein and unless otherwise indicated, the term "prodrug" means a derivative of a compound that can hydrolyze, oxidize, or otherwise react under biological conditions (in vitro or in vivo) to provide the compound of the present invention. For example, the compounds of the present invention encompass esters which may be hydrolyzed to the corresponding alcohols. A thorough discussion is provided in T. Higuchi and V. Stella, Prodrugs as Novel Delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein.

The term "treating", as used herein generally means that the compounds of the invention can be used in humans or animals with at least a tentative diagnosis of disease. The compounds of the invention will delay or slow the progression of the disease thereby giving the individual a more useful life span.

The term "preventing" as used herein means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease.

Compositions of the Present Invention

The present invention contemplates compositions comprising the substantially pure stereoisomers disclosed herein. Preferably, these compositions include pharmaceutical compositions comprising a therapeutically effective amount of one or more of the substantially pure stereoisomers along with a pharmaceutically acceptable carrier.

As used herein, the term "pharmaceutically acceptable carrier" means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Preferred carriers are cyclodextrins, such as Captisol®, and those described in U.S. Pat. Nos. 6,046,177; 5,874,418; 5,376,645; and 5,134,127, which are incorporated by reference.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

By a "therapeutically effective amount" or simply "effective amount" of an active compound, is meant a sufficient amount of the compound to treat or alleviate the negative effects of a neurological disorder or neurodegenerative disease at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

The total daily dose of the active compounds of the present invention administered to a subject in single or in divided doses can be in amounts, for example, from about 0.1 to 100 mg/kg body weight or more usually from 1 to 10 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours.

The compounds of the present invention may be administered alone or in combination or in concurrent therapy with other agents which affect the central or peripheral nervous system, particularly selected areas of the brain.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excrement, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps, and granules. In such solid dosage forms the compounds may be admixed with at least one inert diluent such as sucrose, lactose, or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants, or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active compounds of this invention, excipients such as lactose, talc, silicic acid, aluminum hydroxide, calcium silicates and polyamide powder, or mixtures of these substances. Sprays can additionally contain customary propellants, such as chlorofluorohydrocarbons.

Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Accordingly, the compounds of the present invention are useful in the treatment or alleviation of disease, especially those disorders related to neurological diseases or neurodegenerative disorders, such as Alzheimer's disease, Parkinson's disease, Lou Gehrig's disease, or multiple sclerosis, to name a few, not to mention central or peripheral nervous system damage, dysfunction, or complications involving same stemming from edema, injury, or trauma. Such damage, dysfunction, or complications may be characterized by an apparent neurological, neurodegenerative, physiological, psychological, or behavioral aberrations, the symptoms of which can be reduced by the administration of an effective amount of the active compounds of the present invention.

The following examples are provided for further illustration of the present invention, and do not limit the invention.

EXAMPLE 1

Synthesis of Compounds

General methods. In this example, the para-fluoro (TH-237A, TH-236B, and TH-OPEN) and para-trifluoromethyl (TH-242A, TH-242B, and TH-OPENTFM) compounds were synthesized based on methods for a small synthetic compound as set forth in the scheme below. The $^1$H, $^{13}$C NMR spectra were recorded on a Bruker 400 (400 and 100 MHz respectively) spectrometer. High-resolution mass spectra (HRMS) were obtained on a VG instrument ZAB double-focusing mass spectrometer. The IR spectra were recorded on a Shimadzu FTIR 8400S instrument. Melting points were determined using a Thomas-Hoover melting point apparatus and were uncorrected. Column chromatography was performed employing silica gel (230-400mesh). X-ray diffraction data were collected on the Bruker instrument using Bruker APEX ccd area detector with graphite-monochromated Mo Kα radiation (λ=0.71073 Å). The 4-fluorobenzaldehyde, tris(hydroxymethyl)aminomethane and toluene were bought from Sigma-Aldrich., Milwaukee, Wis. The compound was dissolved in Captisol® (Cydex, Lenexa Kans.) for use in the biological experiments.

Synthetic Methods.

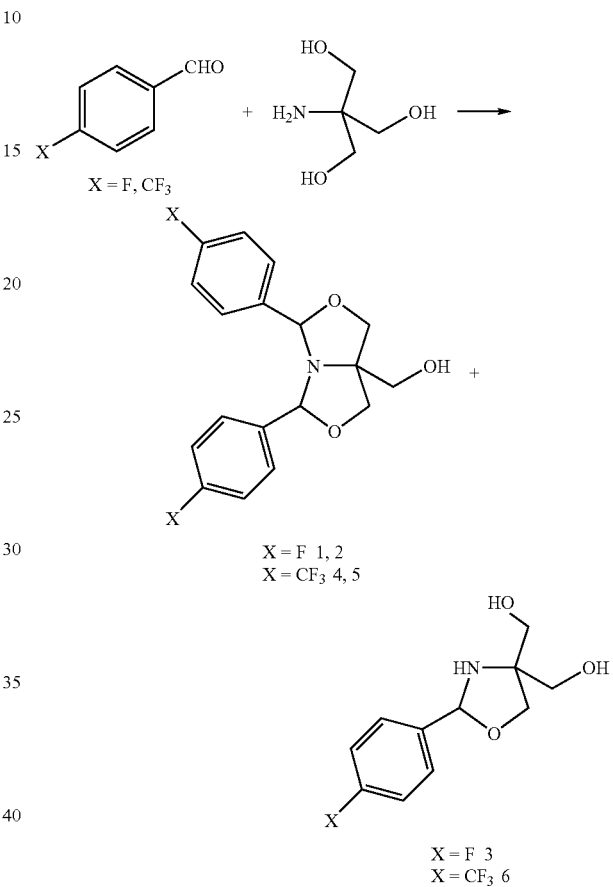

As an example, para-fluorinated compounds were prepared. More specifically, a suspension of 4-fluorobenzaldehyde (27 g, 0.22 mol) and tris(hydroxymethyl)aminomethane (13 g, 0.11 mol) in toluene (350 ml) was heated at reflux temperature with azeotropic removal of water for 12 hours. The reaction mixture was concentrated, stirred at room temperature, and the precipitated, unreacted 4-fluorobenzaldehyde was filtered off. The residue obtained after removal of solvent was subjected to flash chromatography on silica gel using hexane:ethylacetate (4:1 and 1:1). Crystallization of the respective fractions afforded pure compounds TH-237A, TH-236B, and TH-OPEN in yields 66%, 5%, and 21% respectively based on an equimolar product distribution ratio. The structures of the products were assigned by spectral data and the relative stereochemistry of TH-237A was assigned from single crystal X-ray diffraction data. The ellipsoid drawing of the molecular structure TH-237A from X-ray diffraction study is shown in FIG. 1.

(3R,5S,7as)-(3,5-bis(4-fluorophenyl)tetrahydro-1H-oxazolo[3,4-c]oxazol-7a-yl)methanol (TH-237A) (1): Crystallized from hexane as white crystalline solid; mp. 90° C.; IR υcm$^{-1}$ 3444, 2873, 1606, 1504, 1222, 1153, 1078, 1006, 837; $^1$H NMR (400 MHz, CDCl$_3$) δ 3.50 (br s, 2H), 3.94 (d, J=8.9

Hz, 2H), 4.05 (d, J=8.9 Hz, 2H), 5.55 (s, 2H), 7.07 (m, 4H), 7.44 (m, 4H); $^{13}$C NMR (100 MHz, CDCl$_3$) δ 65.63, 72.66, 74.89, 96.65, 115.41, 115.58, 128.55, 128.62, 135.26, 135.29, 161.95, 163.91; HRMS (FAB+) m/z calculated for C$_{18}$H$_{18}$NO$_3$F$_2$ [M+H] 334.1255 found 334.1230.

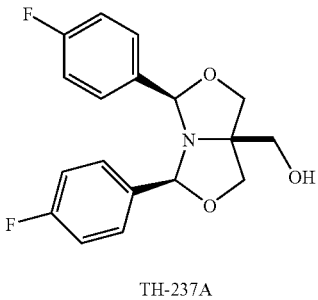

TH-237A (3R,5R) and (3S,5S) (3,5-bis(4-fluorophenyl)tetrahydro-1H-oxazolo[3,4-c]oxazol-7a-yl)methanol (TH-236B) (2): Crystallized from hexane—methylene chloride as white crystalline solid; mp. 115° C.; IR ʋcm$^{-1}$ 3440, 2870, 1606, 1512, 1427, 1384, 1226, 1155, 1076, 837; $^1$H NMR (CDCl$_3$) δ 3.75 (m, 2H), 3.84 (d, J=8.8 Hz, 1H), 3.88 (d, J=8.9 Hz, 1H), 4.10 (d, J=8.9 Hz, 1H), 4.20 (d, J=8.8 Hz, 1H), 5.16 (s, 1H), 5.51 (s, 1H), 6.89 (m, 6H), 7.27 (m, 2H); $^{13}$C NMR (CDCl$_3$) δ 65.60, 72.12, 74.87, 93.03, 93.91, 115.14, 115.31, 115.35, 115.52, 115.78, 129.21, 129.29, 129.34, 129.42, 130.21, 130.24, 135.87, 135.90, 161.89, 164.34; HRMS (FAB+) m/z calcd for C$_{18}$H$_{18}$NO$_3$F$_2$ [M+H] 334.1255 found 334.1237.

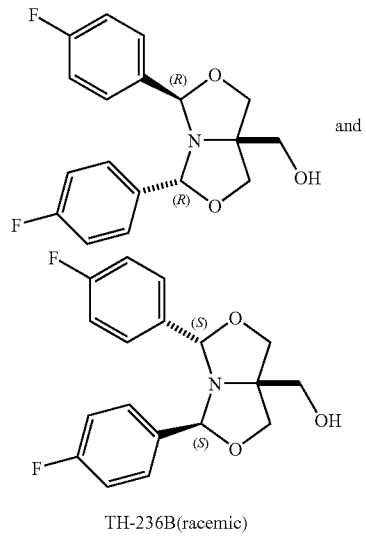

TH-236B(racemic)

(R/S)-(2-(4-fluorophenyl)oxazolidine-4,4-diyl)dimethanol (TH-OPEN) (3): Crystallized from isopropanol as white crystalline solid; mp. 89° C.; IR ʋcm$^{-1}$ 3450, 2877, 1604, 1512, 1420, 1296, 1228, 1157, 1047, 837; $^1$H NMR (CDCl$_3$) δ 3.58 (m, 3H), 3.71 (m, 2H), 3.85 (d, J=8.6 Hz, 1H), 5.41 (s, 1H), 7.06 (m, 2H), 7.44 (m, 2H); $^{13}$C NMR (CDCl$_3$) δ 64.57, 64.98, 67.62, 70.73, 91.79, 115.81, 116.02, 128.29, 128.37, 134.91, 162.17, 164.63; HRMS (FAB+) m/z calcd for C$_{11}$H$_{15}$NO$_3$F [M+H] 228.1036 found 228.1036.

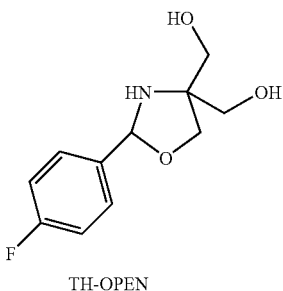

TH-OPEN

As another example, para-trifluoro compounds were prepared. Synthesis of para-trifluoro analogs of was accomplished similar to the synthesis of fluorinated compounds and purified by flash chromatography on silica gel using hexane and ethyl acetate mixture. The products were obtained in yields 15%, 21% and 57% respectively based on equal product distribution ratio.

((3R,5S,7as)-(3,5-bis(4-(trifluoromethyl)phenyl)tetrahydro-1H-oxazolo[3,4-c]oxazol-7a-yl)methanol (TH-242A) (4): Crystallized from hexane—methylene chloride as white crystalline solid; mp. 102° C.; IR ʋcm$^{-1}$ 3470, 2875, 1620, 1326, 1164, 1126, 1066, 1016, 827; $^1$H NMR (CDCl$_3$) δ 3.50 (br s, 2H), 3.94 (d, J=8.9 Hz, 2H), 4.05 (d, J=8.9 Hz, 2H), 5.55 (s, 2H), 7.07 (m, 2H), 7.44 (m, 2H); $^{13}$C NMR (CDCl$_3$) δ 65.98, 73.13, 75.45, 97.17, 123.01, 126.07, 126.10, 127.56, 130.89, 131.21, 131.53, 131.85, 143.78; HRMS (FAB+) m/z calcd for C$_{20}$H$_{18}$NO$_3$F$_6$ [M+H] 434.1191 found 434.1179. The relative stereochemistry was determined by single crystal X-ray diffraction.

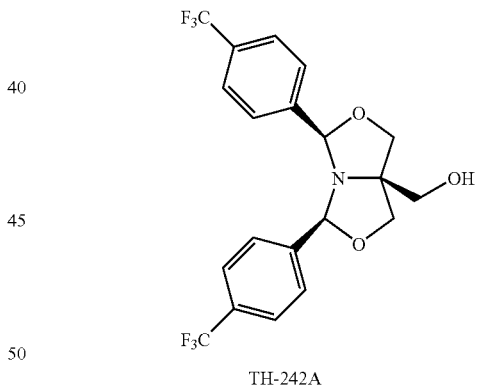

TH-242A (3R,5R) and (3S,5S) (3,5-bis(4-trifluoromethylphenyl)tetrahydro-1H-oxazolo[3,4-c]oxazol-7a-yl)methanol (TH-242B) (5): Crystallized from hexane—methylene chloride as white crystalline solid; mp. 120° C.; IR ʋcm$^{-1}$ 3470, 2875, 1622, 1480, 1427, 1384, 1310, 1218, 1164, 1018, 836; $^1$H NMR (CDCl$_3$) δ 3.73 (m, 2H), 3.84 (t, J=8.8 Hz, 1H), 4.17 (d, J=8.9 Hz, 1H), 4.23 (d, J=8.9 Hz, 1H), 5.16 (s, 1H), 5.59 (s, 1H), 7.08 (d, J=8.0 Hz, 2H), 7.27 (m, 6H); $^{13}$C NMR (CDCl$_3$) δ 65.47, 72.55, 74.95, 75.01, 92.88, 93.77, 125.34, 125.38, 125.42, 125.45, 125.49, 127.87, 127.96, 130.59, 130.92, 131.24, 131.56, 138.23, 143.77; HRMS (FAB+) m/z calcd for C$_{20}$H$_{18}$NO$_3$F$_6$ [M+H] 434.1191 found 434.1180. The relative stereochemistry was determined by single crystal X-ray diffraction.

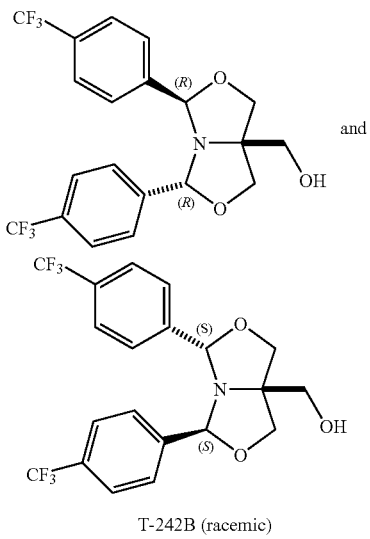

T-242B (racemic)

(R/S)-(2-(4-(trifluoromethyl)phenyl)oxazolidine-4,4-diyl)dimethanol (TH-OPENTFM) (6): Crystallized from ethyl acetate as white crystalline solid; mp. 98° C.; IR $\nu$cm$^{-1}$ 3380, 2880, 1622, 1415, 1326, 1164, 1124, 1068, 1018, 839; $^1$H NMR (CDCl$_3$) δ 3.64 (m, 5H), 3.86 (d, J=8.6 Hz, 1H), 5.50 (s, 1H), 7.63 (m, 4H); $^{13}$C NMR (CDCl$_3$) δ. 64.54, 64.94, 67.69, 70.76, 91.55, 125.91, 125.96, 126.89, 131.20, 131.51, 143.18; HRMS (FAB+) m/z calcd for C$_{12}$H$_{15}$NO$_3$F$_2$ [M+H] 278.1004 found 278.1002.

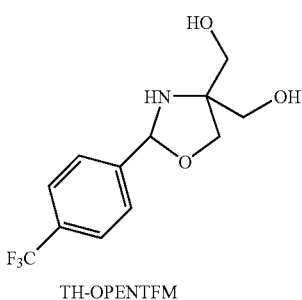

TH-OPENTFM

It will be readily appreciated to those skilled in the art that modification to the starting materials may be made in order to arrive at the compounds of the present invention. For example, use of 4-trifluoromethylbenzaldehyde, 4-difluoromethylbenzaldehyde, 4-fluoromethylbenzaldehyde, 4-chlorobenzaldehyde, 3-fluoromethylbenzaldehyde 3-trifluoromethylbenzaldehyde, 3-difluoromethylbenzaldehyde, 3-fluoromethylbenzaldehyde, 3-chlorobenzaldehyde 2-fluoromethylbenzaldehyde 2-trifluoromethylbenzaldehyde, 2-difluoromethylbenzaldehyde, 2-fluoromethylbenzaldehyde, 2-chlorobenzaldehyde and the like as the starting material will result in the appropriate substitutions on the aromatic rings.

EXAMPLE 2

Neuroprotective Effect of Stereoisomers in Neuronal Cells in Culture after Exposure to Aβ peptides This example illustrates the neuroprotective effects of TH-237A in neuronal cells after exposure to Aβ peptides. To prepare the primary neurons, dissociated cortical cell cultures were established from embryonic day 18 rat festuses recovered from pregnant Sprague Dawley rats (Harlan Sprague Dawley, Inc., Indianapolis, Ind.) as described previously (Michaelis et al., 1994). Pups were delivered by cesarean section while the dam was anesthetized with pentobarbital (140 mg/kg, i.p.), and the brains were recovered according to National Institutes of Health-approved protocols. After the final precipitation step, neurons were suspended in fresh DMEM/F12 (Sigma Chemical Co. St. Louis, Mo.) with 10% fetal bovine serum (Atlanta Biologicals, Atlanta, Ga.) and plated at a density of 2.5×10$^5$ cells in 35 mm glass bottom microwell dishes (Mat-Tek Co., Ashland, Mass.), coated with poly-D-lysine. Serum-containing medium was removed after 24 hours, and the cells were maintained in serum-free DMEM/F12 containing the N$_2$ supplements. Cultures were grown at 37° C. in 5% CO$_2$ and 97% humidity as described (Michaelis et al., 1994).

After five days in culture, the primary neurons were exposed to either Aβ$_{25-35}$ or Aβ$_{1-42}$ in the presence or absence of concentrations of TH-237A ranging from 0.5 to 60 nM. The TH-237A was added about 2 hours before the Aβ peptides. The Aβ$_{25-35}$ was synthesized and purified in the Biochemical Research Services Lab, University of Kansas. The reverse sequence peptide used as a control, Aβ$_{35-25}$, and the Aβ$_{1-42}$ peptide used in confirmatory experiments were purchased from Bachem (Torrance, Calif.). Prior to adding the peptides to the cultures, the Aβ peptide stocks (1.3 mg/ml in double-distilled H$_2$O) were diluted into 10 mM Tris/Cl, pH 7.4, and maintained at about 37° C. for 24 hours. Each batch of Aβ peptide was analyzed for β-sheet formation by circular dichroism, but no effort was made to separate oligomers from fibrils. The peptides were added directly to the culture medium, usually at 10 μM final concentration. Control cultures received the DMSO vehicle alone, and the final concentration of DMSO never exceeded 0.04%. Assays were carried out 48 hours following Aβ peptide addition.

The effects of the Aβ peptides and TH-237A were primarily determined by monitoring neuronal cell survival using the Live/Dead assay as previously described (Michaelis et al., 1998; Michaelis et al., 2005). Following the indicated periods of exposure to the peptides and/or the drugs, cells were labeled with 20 μM propidium iodide (PI) and 150 nM calcein acetoxy-methylester (Molecular Probes, Eugene, Oreg.) for 30 minutes at 37° C. After incubation with the dyes, the dishes were rinsed with phosphate-buffered saline (PBS) and placed on the stage of a Nikon inverted microscope (Nikon Eclipse TE200, Japan) with filters for fluorescein-isothiocyanate and Texas Red. Digital images were captured with a Dage camera and saved in Adobe Photoshop™. The number of viable (green) and dead (red) neurons was determined by counting the cells, and this was done in 6-12 microscopic fields per vulture dish in duplicate dishes for each treatment. All experimental treatments were carried out on at least two separate embryonic neuronal preparations. Thus, approximately 1500 neurons were scored under each treatment condition. The fraction of viable cells in each field was calculated based on the total number of cells counted in each field. Raw data from each experiment were combined and the significance of differences between cultures exposed to various treatments was determined using Student's t test. Neuronal survival in the untreated control samples was considered to represent maximal viability and that in the Aβ-only samples the minimal viability.

Figure 2:
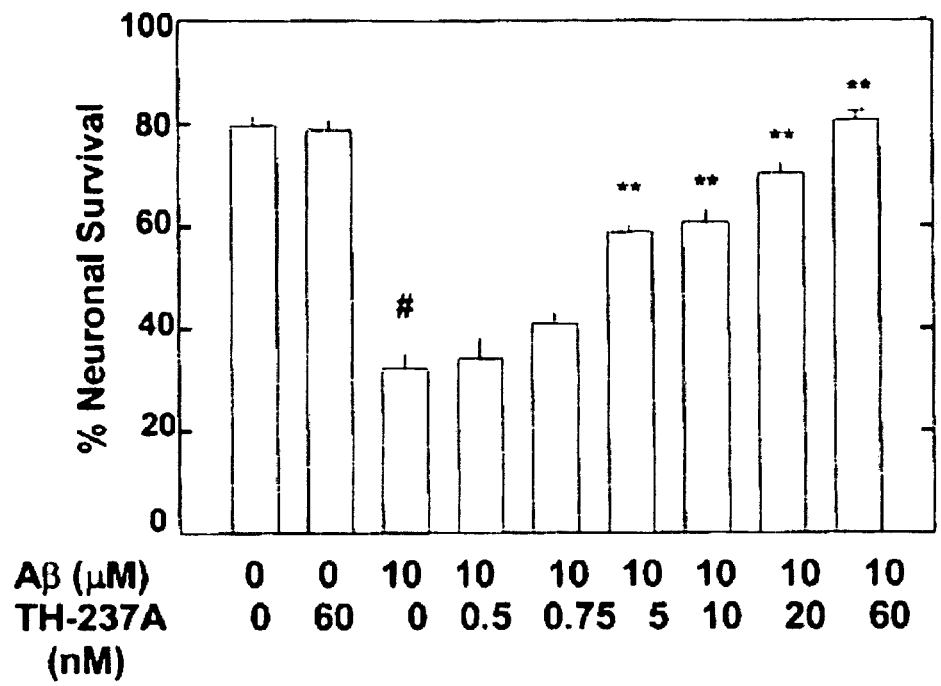
FIG. 2 shows the dose-dependent effects of TH-237A on survival of primary cortical neurons exposed to the toxic Aβ peptide for 48 hours. The % neurons surviving was determined by the Live/Dead assay. Data are from 6 randomly selected fields from 2 neuronal preparations (n=~1,500 cells/condition). Statistical significance was determined by Students t test. #=p<0.001 for controls vs Aβ only. **=p<0.001 for Aβ only vs Aβ+.

FIG. 2 illustrates that TH-237A protected the primary cortical neurons exposed to the toxic Aβ$_{25-35}$ peptides. The EC$_{50}$ for TH-237A (concentration that lead to a 50% increase in neuronal survival in the presence of the Aβ peptide) was 5 nM. Although the small toxic Aβ$_{25-35}$ peptide was used in the majority of studies, the observations were confirmed with exposure to Aβ$_{1-42}$ peptides.

In addition, limited studies involving the racemic TH-236B and the TH-OPEN compound showed the EC$_{50}$ to be about 40 and 50 nM, respectively. Thus, TH-237A clearly exhibited higher neuroprotective effects in vitro.

It is interesting to note that oxazolidines may operate as prodrugs by undergoing hydrolysis in aqueous solutions. This explain in part why TH-OPEN exhibits some degree of neuroprotection comparable to that of TH-236B.

EXAMPLE 3

Neuroprotective Effect of TH-237A in Neuronal Cells in Culture After Exposure to Aβ Peptides Because TH-237A was determined to be the most potent stereoisomer from the previous example, further studies were performed using the stereomerically pure compound. In this example, the effects of neurotoxic stimuli other than Aβ peptides were used to assess protection against various cell-death initiators. Primary neurons were prepared as discussed previously. In this example, staurosporine (100 nM) was used to induce apoptosis, thapsigargin (100 nM) to cause ER stress, and paraquat (25 μM) or hydrogen peroxide (25 μM) to induce oxidative stress. All reagents were obtained from Sigma Chemical Co., St Louis, Mo.

Figure 3:
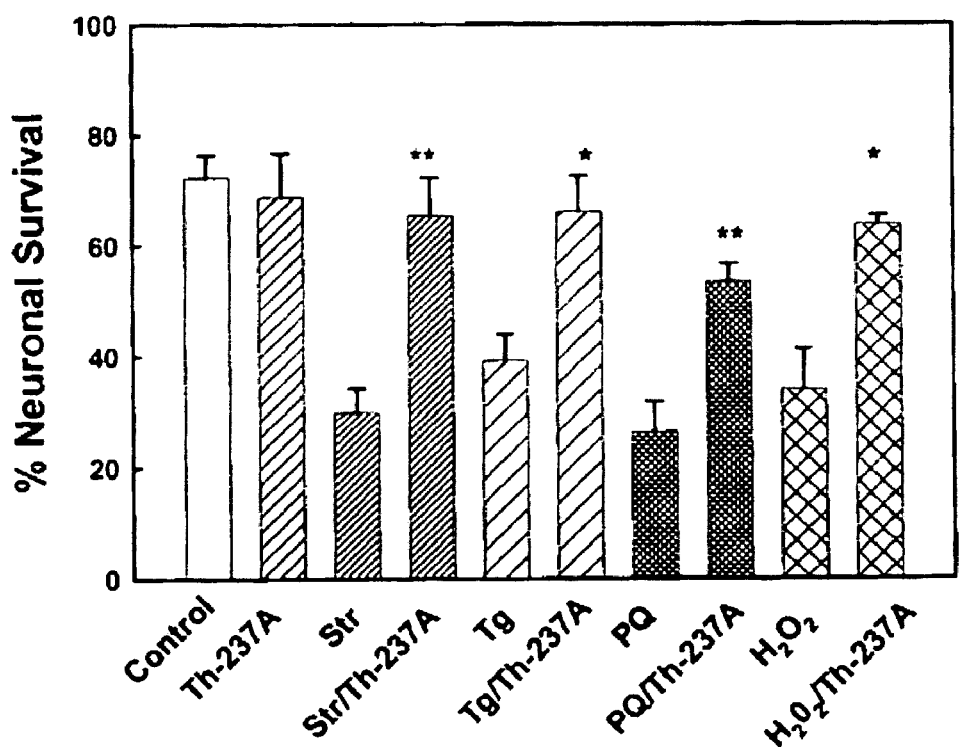
FIG. 3 shows the effects of TH-237A on toxicity induced by diverse stimuli. Primary neurons were exposed to 100 nM staurosporine (Str,), 100 nM Thapsigargin (Tg), 25 µM paraquat (PQ), or 25 µM hydrogen peroxide ($H_2O_2$) with and without 100 nM TH-237A. Mean % survival was determined 24 hours later, and statistical significance was assessed using Student's t test. *=p<0.05 and **=p<0.005 for each toxic stimulus alone vs the toxic stimulus plus the drug. Data are from about 1,000 cells per condition.

TH-237A was added at 100 nM concentration about 2 hours before the toxic stimuli, and cell viability was determined using the Live/Dead assay and obtaining data from multiple fields as described above. The results are illustrated in FIG. 3. Clearly, TH-237A provided neuroprotection for the neuronal cells regardless of the source of the neurotoxic stimuli.

EXAMPLE 4

In Vitro Evaluation of Brain Uptake of Stereoisomers

In this example, the pharmacokinetic properties of TH-237A, racemic TH-236B, and TH-OPEN were investigated for uptake into the brain. Two different methodologies, a rhodamine assay and radiolabeling, were used.

EXAMPLE 4A

Rhodamine Assay

First, a rhodamine 123 assay was used for to assess uptake of the test compound in brain endothelial cells. Bovine brain microvessel endothelial cells ("BBMECs") were isolated and grown in primary culture on 12 well cluster dishes at a density of 50,000 cells/cm$^2$ essentially as described previously (Rice et al., 2005). The culture medium was changed every other day after seeding until a confluent monolayer was formed as determined by light microscopy. Experiments were performed in phosphate buffered saltine supplemented with calcium and glucose (PBSA), pH 7.4. Briefly, the growth medium was first aspirated off, and the cells were rinsed three times with pre-warmed (37° C.) PBSA. The monolayers were then equilibrated either in 1 ml PBSA for 1 hour at 37° C. for control experiments or equilibrated for 30 minutes in PBSA alone, followed by another 45 minutes pre-incubation with the TH-237A. Cyclosporin A (CsA; 10 μM) was used as a known P-glycoprotein inhibitor and as the positive control. Rhodamine 123 accumulation was allowed to proceed for 45 minutes with or without a potential inhibitor present with gentile agitation (about 30 rpm) at 37° C. At the end of the experiment, the drug solution was removed by aspiration and the monolayers were immediately rinsed three times with ice-cold PBSA. Each monolayer was solubilized for 30 minutes (37° C.) with 1 ml of lysing solution (0.5% v/v Triton X-100 in 0.2 N NaOH). Cell lysates were assayed using a microplate fluorescence reader (Bio-Tek Instruments, Winooski, Vt.) at excitation/emission wavelengths of 485 nm/520 nm, then quantified against standard curves of rhodamine 123 in lysing solution. The fluorescence of the cell lysates was corrected for autofluorescence of untreated cells. The protein content of each monolayer was then determined using the BCA protein assay reagent kit. Results were expressed as total nanomoles of rhodamine 123 accumulation per mg cellular protein for agents tested at 10 μM.

| Agent | Rhodamine uptake (nmol/mg protein) |
|---|---|
| TH-237A | 0.21 |
| TH-236B (racemic) | 0.23 |
| TH-OPEN | 0.27 |

The absence of an effect of the TH-237A on rhodamine 123 accumulation indicates the compound is not a substrate for the P-glycoprotein efflux transporter and thus is likely to cross the blood brain barrier. Similarly, racemic TH-236B and TH-OPEN showed the absence of rhodamine 123 accumulation.

In a separate experiment, a trifluromethyl derivative (TH-OPEN) was investigated. This compound had a rhodamine updake of 0.3 nmol/mg protein. Because pharmaceuticals that have little likelihood of entering the brain (e.g. paclitaxel) have rhodamine uptake values of 0.8 or more, the stereoisomers are likely to cross the blood brain barrier.

EXAMPLE 4B

Radiolabeling Experiments

In a separate experiment, the permeation of TH-237A across BBMEC monolayers was demonstrated. The BBMECs were grown on 0.4 μm polycarbonate membranes. After they reached confluency, the cells were transferred to side-by-side diffusion chambers to characterize the transport of radiolabeled TH-237A and Taxol (paclitaxel) across the monolayer. The TH-237A was custom labeled with tritium [$^3$H] by Moravek Biochemicals, Inc. (Brea, Calif.). Transport studies were performed in pH 7.4 standard buffer solutions, consisting of either Hank's balanced salt solution (HBSS) or phosphate buffered saline (PBS) supplemented with 0.63 mM CaCl$_2$, 0.74 mM MgSO$_4$, 5.3 mM glucose and 0.1 mM ascorbic acid (PBSA). Briefly, all studies were performed in 3 ml of PBSA in each donor and receiver chamber of the side-by-side diffusion chambers and stirred at 600 rpm at 37° C. The cells were allowed to equilibrate in PBSA for 30 minutes prior to each experiment and oriented such that apical or blood side of the cells face the donor chamber and the basolateral or brain side of the cells adhere to the polycarbonate membranes and face the receiver chamber of the diffusion apparatus. At each time point, a 100 µl sample was taken from the receiver compartment and immediately replaced with an equal volume of PBSA. The transport studies were performed in the presence or absence of CsA (5-10 µM). Monolayers were checked for trypan blue exclusion after experiments as well to assess general cell viability. The permeability of all monolayers used in these experiments was monitored for [$^{14}$C] sucrose leakage as a measure of potential TH-237A-induced loss of integrity. The radioactivity was quantified using liquid scintillation spectrometry. Apparent permeability coefficients ($P_{app}$) were calculated as $0.5 \times 10^{-5}$ cm/sec for Taxol (paclitaxel), and $27 \times 10^{-5}$ cm/sec for TH-237A.

EXAMPLE 4

In Vivo Pharmacokinetic Evaluation of TH-237A in Plasma and Brain

In this example, the pharmacokinetics of TH-237A were evaluated in vivo. Male Balb/C mice were dosed with TH-237A (10 mg/Kg in Captisol®) via either an i.v. injection into the tail vein or via subcutaneous (sc) injection. At multiple time points ranging from 0 to 240 minutes, 12 mice (n=6, i.v.; n=6, s.c.) were anesthetized with isoflurane, and blood was collected via cardiac puncture. Mice were perfused with 30 mL of saline to wash remaining blood from the vessels, and the brain tissue was harvested. The levels of TH-237A in plasma and brain were quantified using mass spectrometric methods.

Sample preparations. Brain homogenate was prepared in a 1:4 ratio with deionized water. A sonic dismembrator was pulsed at 30% power until the sample was liquified. Aliquots of mouse plasma (0.05 mL) or mouse brain homogenates (0.25 g) were spiked with 50 ng of internal standard (deuterated TH-237A) and vortexed for 10 seconds. The TH-237A and internal standard were extracted using 1.3 mL of methyl t-butyl ether. Samples were vortexed for 5 minutes and centrifuged. The supernatant was transferred to 2 mL centrifuge tubes and evaporated to dryness. The sample was reconstituted in 0.2 mL of sample solvent, vortexed and centrifuged before a 10 uL aliquot was injected on to the LC/MS system for analysis.

Figure 4:
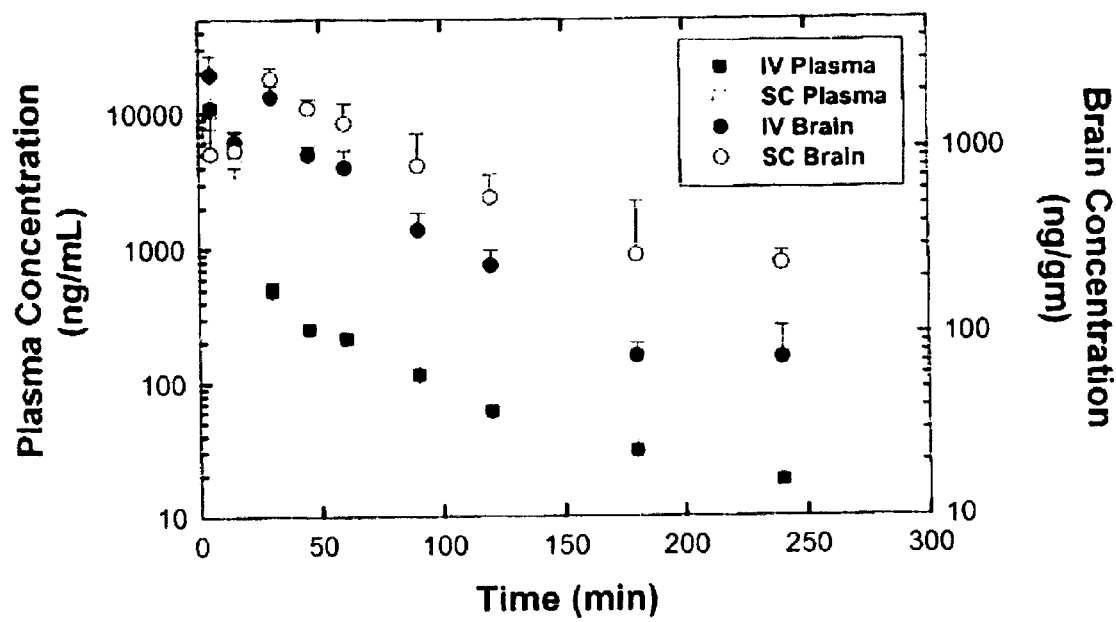
FIG. 4 shows the pharmacokinetic properties of TH-237A followed in plasma and the brain. Male Balb/C mice were dosed with TH-237A (10 mg/kg) via either an i.v. injection into the tail vein (filled squares) or via subcutaneous (sc) injection (open squares). At indicated times, 12 mice (n=6, i.v.; n=6, s.c.) were anesthetized with isoflurane and blood collected via cardiac puncture. Mice were perfused with 30 mL of saline and brain tissue harvested. TH-237A in plasma (left axis) and brain (right axis) was quantified using mass spectrometric methods.

Analysis of TH-237A. The levels of the drug in the samples were determined by means of HPLC/MS. The column was a Gemini-C18, 50×2 mm (Phenomenex, catalogue number 00B-4435-B0, serial number 265528-1). The mobile phase A was 100:0.1 deionized water/formic acid, and the mobile phase B was 20:80:0.1 methanol/acetonitrile/formic acid. Elution was performed using isocratic flow with 47% mobile phase B for 5.5 minutes. The column was rinsed at 80% B at the end of each run and then re-equilibrated at 47%. The flow rate was 0.22 mL/min. The effluent for the first two minutes was diverted to waste. The retention time was 4.5 minutes. The instrument used for the analyses of TH-237A is a Shimadzu LC/MS 2010 system (single quadrapole mass spectrometer used in electrospray positive mode). The results are illustrated in FIG. 4. The plasma levels (ng/mL) of TH-237A over time following administration by either i.v. injection (filled squares) or subcutaneously (open squares) are indicated on the left axis. The brain concentrations of TH-237A (ng/gm) following administration by either i.v. injection (filled circles) or subcutaneously (open circles) are indicated on the right axis. The results of these experiments show that a very significant amount of the drug enters the plasma regardless of route of administration and exhibits a relatively long half-life, on the order of hours. In addition, relatively high brain concentrations of the drug are achieved quite rapidly, and brain levels of approximately 300 nM TH-237A are still present at 4 hours, suggesting the drug is only slowly lost from the brain over time.

EXAMPLE 5

Assessment of TH-237A on Cell Proliferation

In this example, the cytotoxic effects of TH-237A on proliferating cells was investigated using pacitaxel as comparative test compound. MCF-7 human breast cancer and B16 murine melanoma cells in Dulbecco's MEM/F12 medium containing 5% fetal calf serum were plated in 96-well culture plates at a density of 2000 cells per well. After a 24 hours incubation at 37° C. the medium was removed and replaced with fresh medium containing either paclitaxel (Taxol) or TH-237A at varying concentrations ranging between 31 µM and 500 µM. The plates were incubated for 72 hours and the degree of proliferation was measured by staining with sulforhodamine B. The $ED_{50}$ values were obtained by plotting the absorbance at 570 nm against the concentration of the compounds. Taxol had an $ED_{50}$ of 8.7 nM and 2.9 nM in B16 and MCF7 cells, respectively. The $ED_{50}$ of TH-237A was much higher—about 5.5 µM and 12.3 µM in B16 and MCF7 cells. Thus, TH-237A does not have any of the market toxic effects that Taxol has on dividing cells.

A similar experiment was performed on TH-237A, TH-236B, and TH-OPEN on a cancer cell line that overexpresses the drug transporter P-glycoprotein (MCF 7-adr cells). These cells become considerably less sensitive to the drugs because they can pump them out so effectively. The results are shown in the following Table 1:

TABLE 1

| Cytotoxicity Assay in MCF 7-adr Cells | |
|---|---|
| Taxol (paclitaxel) | 1.2 µM |
| TH-237A | 44 µM |
| TH-236B (racemic) | 110 µM |
| TH-OPEN | 130 µM |

Clearly, Taxol is not readily taken up into these MCF 7-adr cells, but the compounds of the present invention are even less permeable in reaching concentrations that can inhibit proliferation. Further, TH-237A does seem to move past the P-glycoprotein transporter more readily than the other two compounds, but very high concentrations of the compounds are required to affect the cell proliferation significantly.

EXAMPLE 6

Investigation of Microtubule-Stabilizing Properties of TH-237A

In this example, the mechanism of TH-237A's neuroprotective effects was investigated. In a first experiment, the microtubule-stabilizing ability of TH-237A was investigated using a tubulin assembly centrifugation assay. Tubulin (1.0 mg/ml), free of microtubule-associated proteins ("MAPs"), was incubated in PEM buffer (0.1 M Pipes, 1 mM EGTA, 1 mM $MgSO_4$, pH 6.9), 4% DMSO, various concentrations of paclitaxel or TH-237A, with or without 0.5 mM GTP, in a total volume of 0.1 ml for 15 minutes at 37° C. Samples were centrifuged at 50,000×g for 4 minutes in a Beckman TL-100 ultracentrifuge. Protein determinations were performed on the supernatants and the amount of polymer formed was calculated from the difference between the starting concentration and the supernatant concentration. The maximum concentration of polymer was taken to be that formed at 25 µM paclitaxel. An experiment was also done using a tubulin preparation containing microtubule-associated proteins ("MTP") at a protein concentration of 2 mg/ml without GTP. The results showed that 75% of tubulin polymerized at 1.0 µM of Taxol, but only 10% of tublin polymerized at 200 µM of TH-237A.

A multi-well plate assay was then performed. This assay depends on the increase in fluorescence when 4',6-diamidino-2-phenylindole (DAPI) binds to microtubules. MTP at 2 mg/ml was used in the absence of GTP and in the presence of 10 µM DAPI. Assays were done in 96-well plates in a 0.1 ml volume. The plates were incubated at 37° C. for 30 minutes after which fluorescence was read on a fluorescence plate reader using an excitation wavelength of 360 nm and an emission wavelength of 460 nm. In the multi-well plate assay, Taxol® was consistently two orders of magnitude more potent than TH-237A in promoting tubulin polymerization.

In another experiment, the cold stability of microtubles was investigated. Microtubules were formed from MAP-free tubulin (2 mg/ml) and MTP (2 mg/ml) at 37° C. A sample was centrifuged at 50,000×g to determine the amount of polymer formed. To three other samples DMSO, 20 µM paclitaxel or 400 µM TH-237A was added, and the samples were placed on ice for 15 minutes before centrifuging at 4° C. Pellets were dissolved in 0.1 ml of 0.1 M NaOH and protein determinations were made on the supernatants and pellets. Cold-induced depolymerization leads to an increase in the supernatant protein concentration. When TH-237A was compared with Taxol in assessing the cold stability of microtubules, Taxol® prevented cold-induced depolymerization of nearly 100% of the microtubules at a concentration of 25 µM, whereas concentrations of TH-237A as high as 400 µM prevented only about 10% of the cold-induced depolymerization of the microtubules.

EXAMPLE 7

Interaction of TH-237A with Microtubules

Binding of $^3$H-TH-237A to microtubules—Microtubules were formed from MTP (2 mg/ml) or from tubulin depleted of MAPs (3 mg/ml) in the presence of 0.5 mM GTP. Various concentrations of either [$^3$H]-paclitaxel or [$^3$H]-TH-237A in a 4 µl volume were added to separate 96 µl aliquot portions of the microtubule suspension. After 10 minutes at 37° C., the microtubules were collected by centrifugation and dissolved in 0.1 ml of 0.1 M NaOH. Protein and radioactivity determinations of the dissolved microtubules were performed.

The radiolabeled TH-237A did bind to the microtubules. However, it required 10 times more TH-237A than Taxol® to achieve a maximal binding level. This indicates that the agent only binds to microtubules at very high concentrations at which non-specific interactions may be occurring.

Competitive binding of paclitaxel and TH-237A—Microtubules were formed from MTP (2 mg/ml) in the presence of 0.5 mM GTP. [$^3$H]-Paclitaxel (4 µl) was added to separate 92 µl aliquot portions of the microtubule suspension, followed by 4 µl aliquot portions of TH-237A solutions. The final concentration of paclitaxel was 20 µM and the TH-237A concentration ranged from 100 to 400 µM. After 10 minutes at 37° C., the microtubules were collected by centrifugation and dissolved in 0.1 ml of 0.1 M NaOH. Protein and radioactivity determinations of the dissolved microtubules were performed.

In the competitive binding assays, very little competition was observed in the displacement of labeled Taxol® (20 µM) by TH-237A, about 15% at a TH-237A concentration of 400 µM. Similarly, when the binding of labeled TH-237A to microtubules was measured at 100 µM concentration, addition of 40 µM Taxol® led to displacement of only about 5% of the bound TH-237A. These data indicate that the two agents do not compete for binding to the same sites on microtubules.

Immunostaining of cellular microtubules—Cells were grown in monolayer on sterile slide cover slips in a 6-well plate and treated with paclitaxel or TH-237A for different periods of time. The cover slips were washed with phosphate-buffered saline and the cells fixed by treatment with 95% EtOH at −20° C. for 30 minutes. The cover slips were placed in a humidified chamber and treated with the primary antibody (a mouse anti-β-tubulin monoclonal antibody) for 2 hours to overnight at room temperature. This was followed by washing with phosphate-buffered saline and treatment with the secondary antibody (FITC goat anti-mouse) for 1 hour at room temperature. Cover slips were examined on a Nikon Optiphot fluorescence microscope.

The polymerization of the microtubules in situ in the cells was clearly evident at 1 and 10 µM Taxol®. No such stabilization was observed in the cells treated with either 50 or 100 µM TH-237A. These observations further indicate TH-237A does not lead to stabilization of the microtubules network in intact cells in the concentration range that led to neuroprotection.

EXAMPLE 9

In Vivo Analysis of TH-237A Treatment in Tau-Mutant Mice

In this example, the in vivo effects of TH-237A in tau-mutant mice were investigated. More specifically, three groups of mice with the P301L tau mutation were as follows: (1) +Tau, mutant mice which had unrestricted access to food and were administered vehicle only, (2) Tau/FR, mutant mice with food restriction (85% of free feed weight), and vehicle only, and (3) Tau/FR/Drug, mutant mice with food restriction (85% of free feed weight), 10 mg/kg of TH-237A (sc administration) daily for 15 weeks. The treatments (FR or FR/drug) were begun at about 5.5 months of age. At 9.5 months, treatment was terminated and the animals were sacrificed. For the +tau mice, severe motor pathology developed, and the mice were sacrificed at about 8.5 months.

Figure 5:
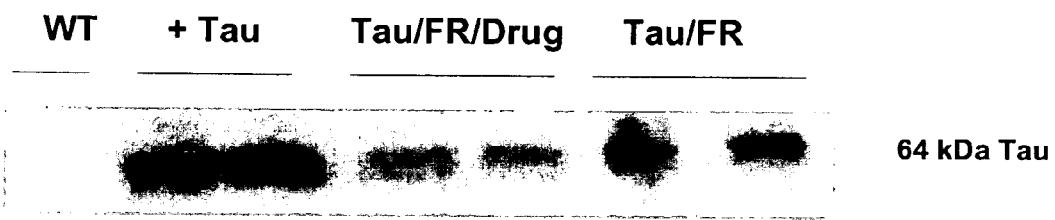
FIG. 5 is an immunoblot of abnormal tau labeled with AT8 antibodies. The blot shows representative data from 2 different animals in each group. In addition, a non-transgenic, wild-type mouse that does not have any hyperphosphorylated tau is shown.
Figure 6A:
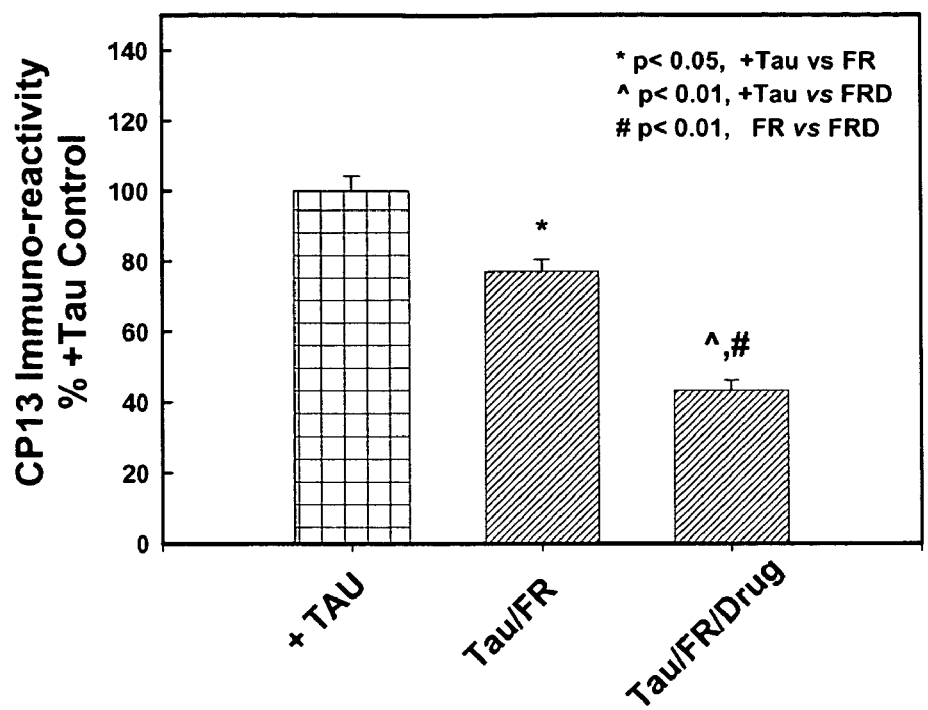
FIGS. 6(a)-(c) quantifies the P3 fraction labeling with antibodies AT8, Cp13, and PHF1 from P3 fractions from the brain. The data are mean +/− SE(+Tau=5 mice, Tau/FR=7 mice, Tau/FR/Drug=7 mice).
Figure 6B:
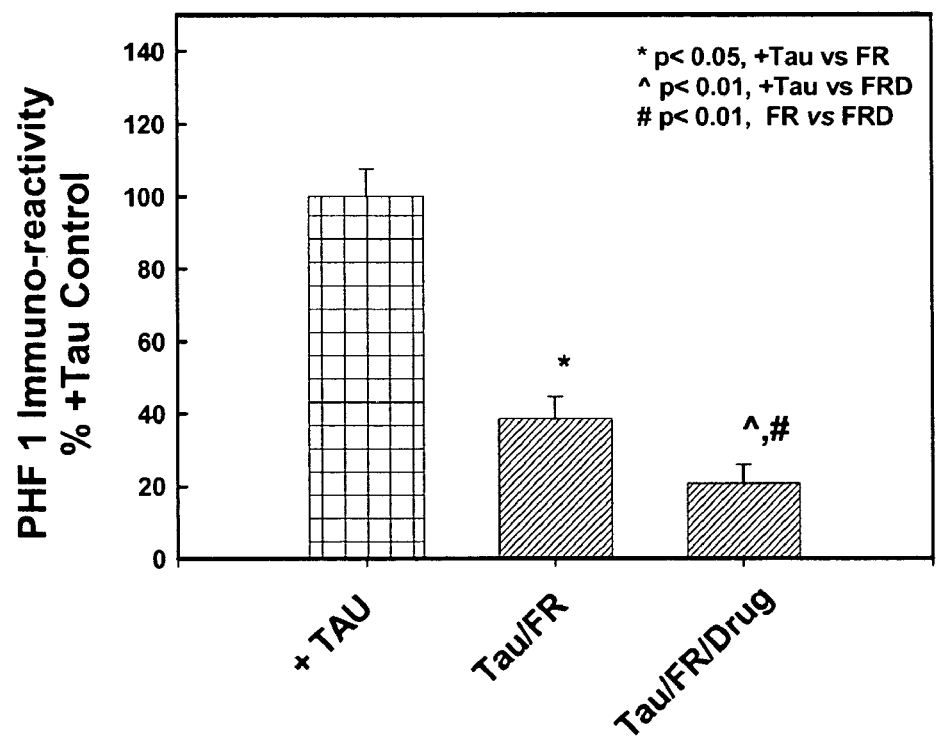
Figure 6C:
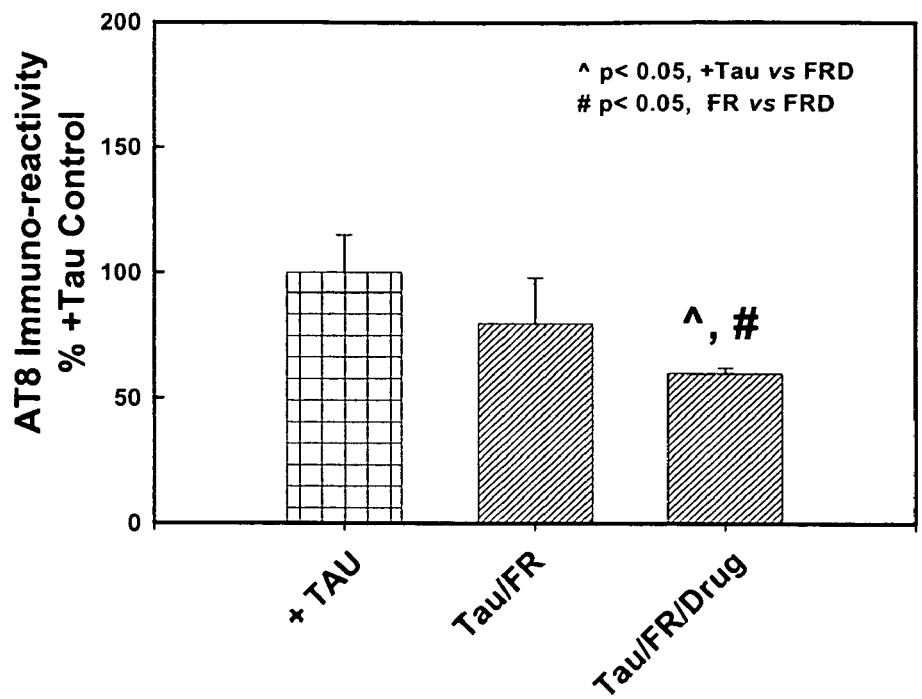
Figure 7A:
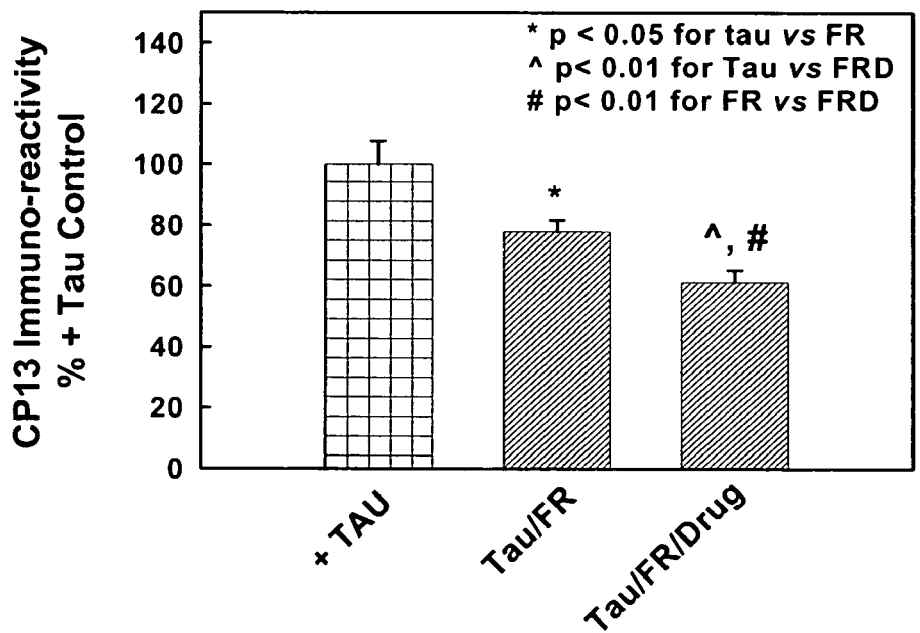
FIGS. 7(a)-(c) quantifies the P3 fraction labeling with antibodies AT8, Cp13, and PHF1 from P3 fractions from the spinal cord. The data are mean +/− SE(+Tau=2 mice, Tau/FR=7 mice, Tau/FR/Drug=7 mice).
Figure 7B:
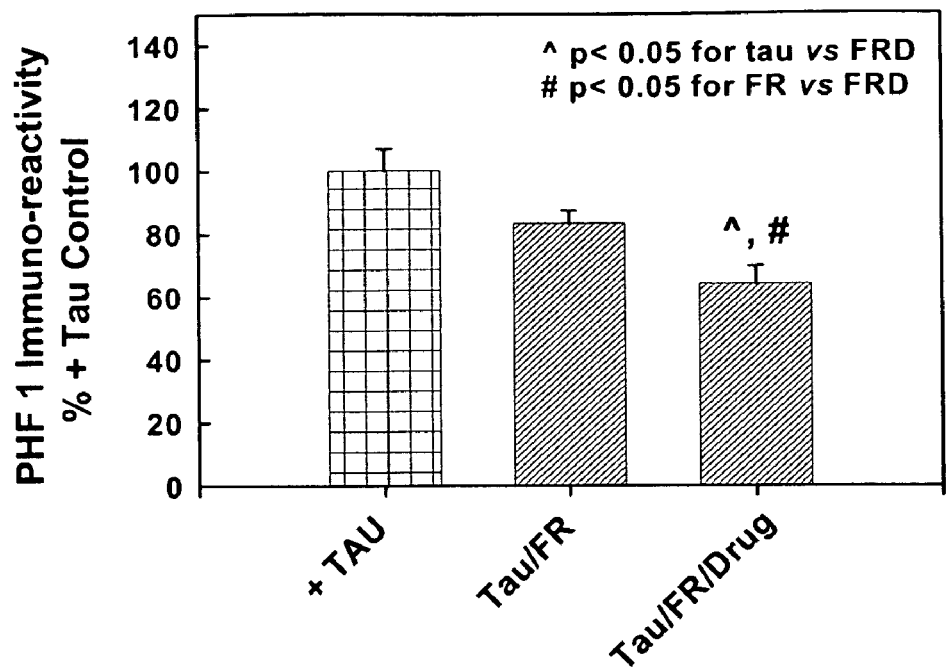
Figure 7C:
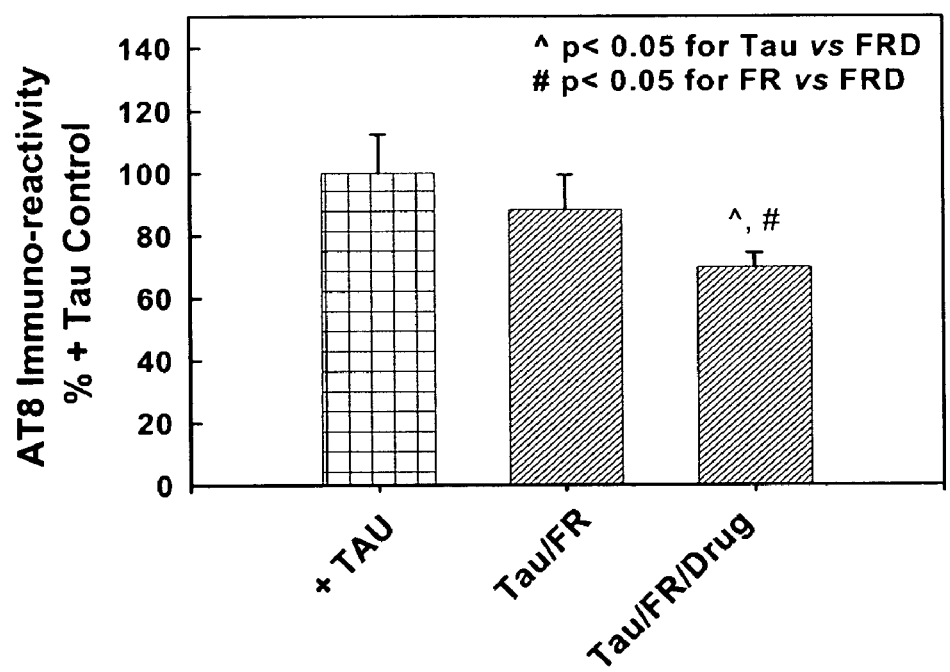

To evaluate the effect of TH-237A on pathology, biochemical indicators of abnormal tau were investigated using immunoblot and densitometery. Three antibodies that selectively react with hyper-phosphorylated insoluble tau were used, CP13, PHF1, and AT8. The mouse brains and spinal cords were recovered, subfractionated, and the sarkosyl-insoluble P3 fractions were isolated and run on SDS-PAGE followed by immunoblot analysis. The 64 kDa abnormal tau band was labeled using the antibodies as shown in FIG. 5. The relative results of the antibody labeling are shown in FIGS. 6(a)-(c) for the brain and FIG. 7(a)-(c) for the spinal cord. As expected, the +Tau mice showed strong P3 labeling with all three antibodies to the abnormal tau. The tau mutant mice on food restriction did not develop motor pathology prior to sacrifice at age 9.5 months. The tau mutant mice on food restriction also had less brain and spinal cord labeling of abnormal tau when sacrificed. The tau mutant mice on food restriction given the TH-237A did not develop motor pathology, but showed significantly less labeling of abnormal tau that the FR-only mice. Thus, although food restriction slowed the appearance of motor, spinal cord, and brain pathology, chronic treatment with TH-237A slowed the disease progression even more significantly. Thus, this experiment suggests an in vivo neuroprotective effect associated with TH-237A.

REFERENCES CITED

The publications and other materials used herein to illuminate the background of the invention or provide additional details respecting the practice, are incorporated by reference.

Burr et al, *Prodrugs as drug delivery systems 66. Hydrolysis of various oxazolidines and N-acylated oxazolidines—potential prodrug types for β-aminoalcohols or carbonyl containing drugs*, Arch. Pharm. Chem., Sci. Ed. (1987), 15, 76-86.

Michaelis M L, Walsh J L, Pal R, Hurlbert M, Hoel G, Bland K, Foye J, Kwong WH (1994) *Immunologic localization and kinetic characterization of a Na+/Ca2+ exchanger in neuronal and non-neuronal cells*, Brain Res 661:104-116.

Michaelis M L, Ranciat N, Chen Y, Bechtel M, Ragan R, Hepperle M, Liu Y, Georg G (1998) *Protection against beta-amyloid toxicity in primary neurons by paclitaxel (Taxol)*, J Neurochem 70:1623-1627.

Michaelis M L, Ansar S, Chen Y, Reiff E R, Seyb K I, Himes R H, Audus K L, Georg G I (2005) *Beta-Amyloid-induced neurodegeneration and protection by structurally diverse microtubule-stabilizing agents*, J Pharmacol Exp Ther 312:659-668.

Rice A, Liu Y, Michaelis M L, Himes R H, Georg G I, Audus K L (2005) *Chemical modification of paclitaxel (Taxol) reduces P-glycoprotein interactions and increases permeation across the blood-brain barrier in vitro and in situ*, J Med Chem 48:832-838.

Shintani Y, Tanaka T, Nozaki Y (1997) *GS-164, a small synthetic compound, stimulates tubulin polymerization by a similar mechanism to that of Taxol*, Cancer Chemother Pharmacol 40:513-520.

Shintani et al., Pharmaceutical compositions, microtubule polymerization accelerators, cell proliferation inhibitors, and antitumour agents containing 3,7-dioxa-1-azabicyclo[3,3,0] octane, Japan Patent JP 08325147 (1996).

From the foregoing it will be seen that this invention is one well adapted to attain all ends and objectives herein-above set forth, together with the other advantages which are obvious and which are inherent to the invention. Further, since many possible embodiments may be made of the invention without departing from the scope thereof, it is to be understood that all matters herein set forth are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed:

1. A stereomerically pure compound according to Formula I:

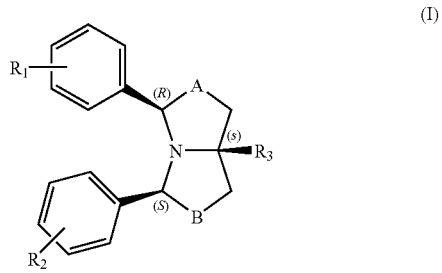

wherein A and B are sulfur or oxygen;
wherein $R_1$ and $R_2$ are independently halogen, alkyl, alkoxy, haloalkyl; and
wherein $R_3$ is alcohol.

2. The stereomerically pure compound according to Formula I of claim 1 wherein A and B are both oxygen, and wherein $R_1$ and $R_2$ are both in the para position according to:

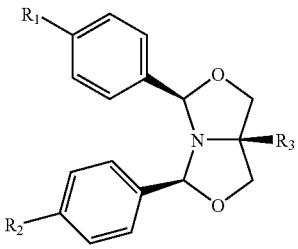

wherein $R_1$ and $R_2$ are independently halogen, alkyl, alkoxy, haloalkyl; and
wherein $R_3$ is alcohol.

3. The stereomerically pure compound according to claim 2 which is selected from
(3R, 5S,7as)-(3,5-bis(4-fluorophenyl)tetrahydro-1H-oxazolo[3,4-c] oxazol-7a-yl)methanol (TH-237A);
(3R, 5S,7as)-(3,5-bis(4-trifluoromethylphenyl)tetrahydro-1H-oxazolo[3,4-c] oxazol-7a-yl)methanol (TH-242A);
(3R, 5S,7as)-(3,5-bis(4-difluoromethylphenyl)tetrahydro-1H-oxazolo[3,4-c]oxazol-7a-yl)methanol;
(3R, 5S,7as)-(3,5-bis(4-fluoromethylphenyl)tetrahydro-1H-oxazolo[3,4-c]oxazol-7a-yl)methanol;
(3R, 5S,7as)-(3,5-bis(4-chlorophenyl)tetrahydro-1H-oxazolo[3,4-c]oxazol-7a-yl)methanol;
(3R, 5S,7as)-(3,5-bis(4-methylphenyl)tetrahydro-1H-oxazolo[3,4-c]oxazol-7a-yl)methanol;
(3R, 5S,7as)-(3,5-bis(4-methoxyphenyl)tetrahydro-1H-oxazolo[3,4-c]oxazol-7a-yl)methanol;
(3R, 5S,7as)-(3,5-bis(4-fluorophenyl)tetrahydro-1H-oxazolo[3,4-c]oxazol-7a-yl)ethanol;
(3R, 5S,7as)-(3,5-bis(4-trifluoromethylphenyl)tetrahydro-1H-oxazolo[3,4-c]oxazol-7a-yl)ethanol;
(3R, 5S,7as)-(3,5-bis(4-difluoromethylphenyl)tetrahydro-1H-oxazolo[3,4-c]oxazol-7a-yl)ethanol;
(3R, 5S,7as)-(3,5-bis(4-fluoromethylphenyl)tetrahydro-1H-oxazolo[3,4-c]oxazol-7a-yl)ethanol;
(3R, 5S,7as)-(3,5-bis(4-chlorophenyl)tetrahydro-1H-oxazolo[3,4-c]oxazol-7a-yl)ethanol;

(3R, 5S,7as)-(3,5 -bis(4-methylphenyl)tetrahydro-1H-oxazolo[3,4-c]oxazol-7a-yl)ethanol; and (3R, 5S,7as)-(3,5 -bis(4-methoxyphenyl)tetrahydro-1H-oxazolo[3,4-c]oxazol-7a-yl)ethanol.

4. The stereomerically pure compound according to Formula I of claim 1 wherein A and B are both oxygen, and $R_1$ and $R_2$ are both in the meta position.

5. The stereomerically pure compound according to claim 4 which is selected from
(3R, 5S,7as)-(3,5-bis(3-fluorophenyl)tetrahydro-1H-oxazolo[3,4-c]oxazol-7a-yl)methanol;
(3R, 5S,7as)-(3,5-bis(3-trifluoromethylphenyl)tetrahydro-1H-oxazolo[3,4-c]oxazol-7a-yl)methanol;
(3R, 5S,7as)-(3,5-bis(3-difluoromethylphenyl)tetrahydro-1H-oxazolo[3,4-c]oxazol-7a-yl)methanol;
(3R, 5S,7as)-(3,5-bis(3-fluoromethylphenyl)tetrahydro-1H-oxazolo[3,4-c]oxazol-7a-yl)methanol;
(3R, 5S,7as)-(3,5-bis(3-chlorophenyl)tetrahydro-1H-oxazolo[3,4-c]oxazol-7a-yl)methanol;
(3R, 5S,7as)-(3,5-bis(3-methylphenyl)tetrahydro-1H-oxazolo[3,4-c]oxazol-7a-yl)methanol;
(3R, 5S,7as)-(3,5-bis(3-methoxyphenyl)tetrahydro-1H-oxazolo[3,4-c]oxazol-7a-yl)methanol;
(3R, 5S,7as)-(3,5-bis(3-fluorophenyl)tetrahydro-1H-oxazolo[3,4-c]oxazol-7a-yl)ethanol;
(3R, 5S,7as)-(3,5-bis(3-trifluoromethylphenyl)tetrahydro-1H-oxazolo[3,4-c]oxazol-7a-yl)ethanol;
(3R, 5S,7as)-(3,5-bis(3-difluoromethylphenyl)tetrahydro-1H-oxazolo[3,4-c]oxazol-7a-yl)ethanol;
(3R, 5S,7as)-(3,5-bis(3-fluoromethylphenyl)tetrahydro-1H-oxazolo[3,4-c]oxazol-7a-yl)ethanol;
(3R, 5S,7as)-(3,5-bis(3-chlorophenyl)tetrahydro-1H-oxazolo[3,4-c]oxazol-7a-yl)ethanol;
(3R, 5S,7as)-(3,5-bis(3-methylphenyl)tetrahydro-1H-oxazolo[3,4-c]oxazol-7a-yl)ethanol; and
(3R, 5S,7as)-(3,5-bis(3-methoxyphenyl)tetrahydro-1H-oxazolo[3,4-c]oxazol-7a-yl)ethanol.

6. The stereomerically pure compound according to Formula I of claim 1 wherein A and B are both oxygen, and $R_1$ and $R_2$ are both in the ortho position.

7. A stereomerically pure compound according to claim 6 which is selected from
(3R,5S,7as)-(3,5-bis(2-fluorophenyl)tetrahydro-1H-oxazolo[3,4-c]oxazol-7a-yl)methanol;
(3R, 5 S, 7as)-(3 , 5 -bis(2-trifluoromethylphenyl)tetrahydro- 1 H-oxazolo[3 , 4-c] oxazol-7a-yl)methanol;
(3R,5S,7as)-(3,5-bis(2-difluoromethylphenyl)tetrahydro-1H-oxazolo[3,4-c]oxazol-7a-yl)methanol;
(3R,5S,7as)-(3,5-bis(2-fluoromethylphenyl)tetrahydro-1 H-oxazolo[3,4-c]oxazol-7a-yl)methanol;
(3R,5S,7as)-(3,5-bis(2-chlorophenyl)tetrahydro-1H-oxazolo[3,4-c]oxazol-7a-yl)methanol;
(3R,5S,7as)-(3,5-bis(2-methylphenyl)tetrahydro-1H-oxazolo[3,4-c]oxazol-7a-yl)methanol;
(3R,5S,7as)-(3,5-bis(2-methoxyphenyl)tetrahydro-1H-oxazolo[3,4-c]oxazol-7a-yl)methanol;
(3R,5S,7as)-(3,5-bis(2-fluorophenyl)tetrahydro-1H-oxazolo[3,4-c]oxazol-7a-yl)ethanol;
(3R,5S,7as)-(3,5-bis(2-trifluoromethylphenyl)tetrahydro-1H-oxazolo[3,4-c]oxazol-7a-yl)ethanol;
(3R,5S,7as)-(3,5-bis(2-difluoromethylphenyl)tetrahydro-1H-oxazolo[3,4-c]oxazol-7a-yl)ethanol;
(3R,5S,7as)-(3,5-bis(2-fluoromethylphenyl)tetrahydro-1H-oxazolo[3,4-c]oxazol-7a-yl)ethanol;
(3R,5S,7as)-(3,5-bis(2-chlorophenyl)tetrahydro-1H-oxazolo[3,4-c]oxazol-7a-yl)ethanol;
(3R,5S,7as)-(3,5-bis(2-methylphenyl)tetrahydro-1H-oxazolo[3,4-c]oxazol-7a-yl)ethanol; and
(3R,5S,7as)-(3,5-bis(2-methoxyphenyl)tetrahydro-1H-oxazolo[3,4-c]oxazol-7a-yl)ethanol.

8. The stereomerically pure compound according to Formula I of claim 1 wherein A and B are both oxygen, and $R_1$ and $R_2$ are independently in the para position, meta position, and ortho position, but $R_1$ and $R_2$ are not both para, both meta, or both ortho.

9. A method of treating neurodegenerative disorder wherein the disorder is Alzheimer's in a patient comprising administering to a patient in need of such treatment a therapeutically effective amount of stereomerically pure compound according to Formula I:

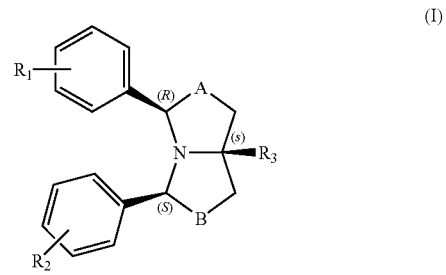

wherein A and B are sulfur or oxygen;
wherein $R_1$ and $R_2$ are independently halogen, alkyl, alkoxy, haloalkyl; and
wherein $R_3$ is alcohol.

10. The method of claim 9 wherein the stereomerically pure compound is (3R, 5S,7as)-(3,5 -bis(4-fluorophenyl)tetrahydro- 1H-oxazolo[3,4-c]oxazol-7a-yl)methanol (TH-237A) or a pharmaceutically acceptable prodrug thereof.

11. The method of claim 10 wherein said stereomerically pure (3R,5S,7as)-(3,5-bis(4-fluorophenyl)tetrahydro-1H-oxazolo[3,4-c]oxazol-7a-yl)methanol (TH-23 7A) is administered parenterally, transdermally, mucosally, nasally, buccally, sublingually, or orally.

12. The method of claim 10 wherein said stereomerically pure (3R,5S,7as)-(3,5-bis(4-fluorophenyl)tetrahydro-1H-oxazolo[3,4-c]oxazol-7a-yl)methanol (TH-237A) is complexed with a cyclodextrin as a pharmaceutically acceptable carrier.

13. The method of claim 9 wherein the patient is a mammal.

14. The method of claim 9 wherein the therapeutically effective amount is from about 1 to 100 mg/kg per day.

15. The method of claim 9 wherein the stereomerically pure compound is (3R,5S,7as)-(3,5 -bis(4-fluorophenyl)tetrahydro-1H-oxazolo[3,4-c]oxazol-7a-yl)methanol (TH-242A) or a pharmaceutically acceptable prodrug thereof.

16. The method of claim 9 wherein said stereomerically pure compound does not stabilize microtubules.

17. A pharmaceutical composition comprising stereomerically pure compound according Formula I and a pharmaceutically acceptable carrier

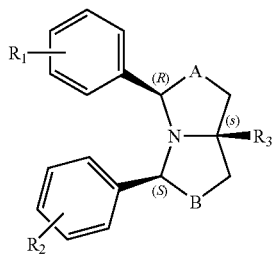

(I)

wherein A and B are sulfur or oxygen;
wherein $R_1$ and $R_2$ are independently halogen, alkyl, alkoxy, haloalkyl; and
wherein $R_3$ is alcohol.

18. The pharmaceutical composition of claim 17 wherein the stereomerically pure compound is (3R,5S,7as)-(3,5-bis (4-fluorophenyl)tetrahydro-1H-oxazolo[3,4-c]oxazol-7a-yl) methanol (TH-237A) or (3R,5S,7as)-(3,5-bis(4-trifluoromethylphenyl)tetrahydro- 1H-oxazolo[3,4-c]oxazol-7a-yl) methanol (TH-242A).

19. A pharmaceutical composition comprising stereomerically pure compound according the following formula and a pharmaceutically acceptable carrier wherein the carrier is a cyclodextrin,

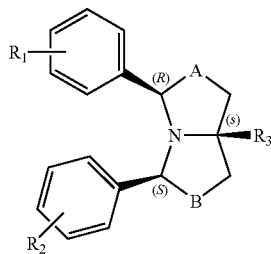

(I)

wherein A and B are sulfur or oxygen;
wherein $R_1$ and $R_2$ are independently halogen, alkyl, alkoxy, haloalkyl; and
wherein $R_3$ is alcohol.

* * * * *